(12) United States Patent
Steinman

(10) Patent No.: US 10,623,876 B1
(45) Date of Patent: Apr. 14, 2020

(54) DEVICE FOR REDUCING TINNITUS POTENTIAL

(71) Applicant: Gary David Steinman, Jerusalem (IL)

(72) Inventor: Gary David Steinman, Jerusalem (IL)

( * ) Notice: Subject to any disclaimer, the term of this patent is extended or adjusted under 35 U.S.C. 154(b) by 0 days.

(21) Appl. No.: 16/602,089

(22) Filed: Aug. 5, 2019

(51) Int. Cl.
 *H04R 25/00* (2006.01)
 *A61F 11/08* (2006.01)

(52) U.S. Cl.
 CPC ........ *H04R 25/75* (2013.01); *A61F 2011/085* (2013.01)

(58) Field of Classification Search
 CPC ..... H04R 25/75; A61F 2011/085; A61F 11/08
 See application file for complete search history.

(56) References Cited

U.S. PATENT DOCUMENTS

| 10,045,133 B2 * | 8/2018 | Bauman | G10K 11/16 |
| 2006/0042868 A1 * | 3/2006 | Berg | A61F 11/08 |
| | | | 181/135ke |
| 2010/0135502 A1 * | 6/2010 | Keady | A61B 5/121 |
| | | | 381/58 |

* cited by examiner

*Primary Examiner* — Mark Fischer

(57) ABSTRACT

The potential to develop disturbing tinnitus may result from repeated unprotected exposure to loud sounds such as rock concerts, machinery, automobile traffic, and crowds at sporting events. Older adults, especially above the age of 50, may be more susceptible to tinnitus resulting from pathologic conditions in the inner ear apparatus. The present device is designed to electronically reduce stressed hearing during the auditory insult and to return to normal function when the insult is removed. No manual adjustment by the user is necessary between these phases. This device is miniaturized to allow wearing it in the outer ear canal during periods of sound excesses and removal at other times. Unlike prior auditory aids, this one acts to block loud noises without the need to remember to place or activate auxiliary devices such as ear plugs to protect against or compete with potentially destructive external factors each time an insult is encountered.

1 Claim, 2 Drawing Sheets

DEVICE FOR REDUCING TINNITUS POTENTIAL

REFERENCES CITED [REFERENCED BY]

U.S. Patent Documents

Figure 1:
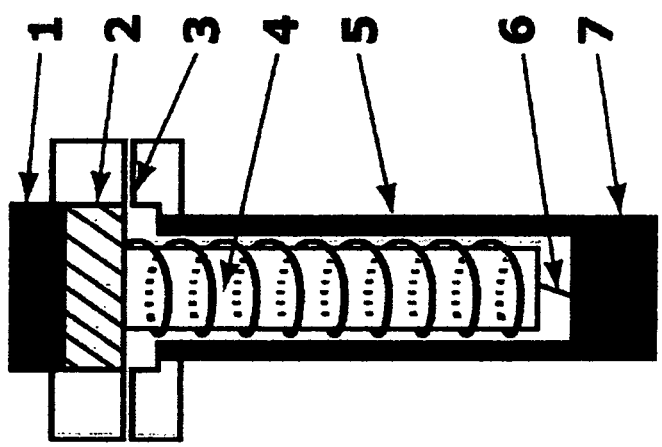

U.S. Pat. No. 4,984,579 January 1991 Burgert et al
U.S. Pat. No. 625,162 June 2001 Leysieffer
U.S. Pat. No. 7,347,827 March 2008 Choy
U.S. Pat. No. 8,976,990 March 2015 Pontoppidan et al
U.S. Pat. No. 9,420,389 August 2016 Pontoppidan
U.S. Pat. No. 9,712,933 July 2017 Pontoppidan U.S. Patent Applications 20190167985 June 2019 Carlson Other References 1) Okamoto et al. "Listening to tailor-made notched music reduces tinnitus loudness and tinnitus-related auditory cortex activity", PNAS, vol. 107, No. 3, pp. 1207-1210 (2010).
2) Tyler et al. "Tinnitus and hyperacusis", in Handbook of Clinical Audiology, J. Katz, ed., chapter 35, pp. 647-658, Wolters Kluwer, 7$^{th}$ edition, 2015.

BACKGROUND OF THE INVENTION

Field of the Invention

Tens of millions of Americans (and many more non-Americans) suffer from tinnitus, a condition of the human auditory system which translates air-transmitted sound to the ear, where it is converted by the inner cochlea to nerve impulses. These impulses are deciphered in the brain to what is recognized as hearing. Damage to the hair-like elements of the inner ear cochlea by disease, excessive noise, or injury to middle ear blood flow or muscle contraction, may lead to persistent or intermittent background sounds known as tinnitus (for unknown reasons). Hearing capacity may also be reduced. Whereas some instances of tinnitus result from ear infections, Meniere's Disease, injuries, sudden onset of short-term deafness, acoustic neuroma, atherosclerosis, hypertension, or drug abuse, the majority of cases in seniors are a consequence of aging. In younger patients, the onset of tinnitus can usually be traced to exposure to excessive, prolonged noise. Although unsubstantiated claims of cure have been made, to date there is no well-documented permanent elimination of this medical problem. In some cases, the tinnitus buzzing sound is continuous and in others it is intermittent, especially after exposure to loud noise.

Description of Related Art

As a protective device, ear plugs made of silicon or sponge lubber, as well as sound-blocking large earphones, offer a degree of isolation from loud noises. The error in using this method usually relates to forgetting to apply them before the noise is apparent. Recurrent use of topical steroids or medications usually does not lead to cure.

A number of hearing aid formats also incorporate white noise production or increased air pressure within the canal to override the sound of tinnitus, but in most cases this is only partially effective:

U.S. Pat. No. 4,984,579—This patent describes a self-treatment of cases of tinnitus already in existence, rather than a means for preventing the initiation of this disorder, by employing forced air. The use of an external pump to achieve this treatment would not make it portable and in continuous use, as in the present application.

U.S. Pat. Nos. 6,251,062, 7,347,827, 8,976,990, 9,420,389, and 9,712,933, employ externally generated sound delivering systems which attempt to camouflage the frequencies of existing cases of tinnitus. US Patent Application 20190167985 uses implantable electrodes for this purpose. In contradistinction, the present application describes a simple device to serve as a means to reduce exposure to loud noise to prevent the appearance of tinnitus de novo, when correctly and diligently applied.

BRIEF SUMMARY OF THE INVENTION

The present invention consists of a means for opening/closing the sound passage of an ear canal tube using an electromagnet controlled by a sound sensor. The sound sensor is activated when the surrounding sound is greater than 85 decibels, thereby closing the sound passageway of the device. Below this level, the electromagnet is deactivated ("off") and the passageway is open to normal hearing. The device can remain in the ear canal in either position, unless an irritation develops. In the "off" (closed) position, the intensity of the perceived sound is about 10% of that in the proximate external environment at that moment (see FIG. 1).

[It is important to realize that the device described here is only one example of a modality which can provide an on/off system that is activated when a loud external noise arises and deactivated when it recedes. Each of the design and performance variations possible can have larger or smaller measurements, numerous means of sound reception at a range of wavelengths to govern the patency of the communicating passage, a number of materials to provide a means for opening and closing the connection between the external environment and the ear canal, and a range of appropriate materials for constructing the device.]

DETAILED DESCRIPTION OF THE INVENTION

Tinnitus is a condition which affects many people. Once established, it is usually impossible to eliminate completely in most cases. If attacks of the buzzing or whistling sound characteristic of tinnitus can be minimized early in the course of the problem, it is conceivable that the intensity and frequency of such events can be held low. The therapeutic key in many cases is reducing the exposure to loud noises before permanent damage to the hair cells of the cochlea results. Ear plugs or muffling headphones are commonly used for this purpose. However, users often forget to insert them before such exposure, thereby defeating the purpose of this approach. The intent in the present invention is to have this potential in place prior to an episode of need.

The basic design of the present invention is a cylindrical plastic ear device with an open sound passageway except when loud noises occur in its vicinity. The sound sensor of the posterior (external) end induces its battery-operated electromagnet to function as a mechanical solenoid, whereby the inner plunger descends and is attracted to the ferrous ring in the bottom (internal) end of the plug, thereby closing the sound channel. After the noise dissipates, the electromagnet shuts down and the spring in the bottom of the shaft forces the plunger upward, into the open position.

There is no need to remove the device immediately unless there is certainty that no more noisy events will occur in the vicinity. During a music concert or a noisy work activity, the device should remain in the ear canal. A small amount of inert lubricating jelly on the internal end, aids insertion.

The cylindrical-shaped device is commonly 0.2-0.8 centimeter in diameter and 1.2-5.0 centimeters in length based on the anticipated size of potential users. The body of the device can be prepared from firm workable material to which human tissue is unreactive. Larger and smaller dimensions are practicable as well, depending on the user's canal size. If needed, the circular, flat battery is replaceable once the sound sensor is removed. The voltage of the battery is determined by the size of the device and the level of energy needed to effect electromagnet motion of the internal plunger. An appropriate alternative to this would be an external handle which could be used to move the plunger, but this would eliminate the automatic feature of the device described above. Practitioners proficient in the art are able to employ variations of design, material, and size to achieve the desired benefit.

Advantages of the Device

1) Able to be retained in outer ear canal or by an external ear clip.
2) Meant to prevent tinnitus or to keep it from getting worse.
3) No effect on hearing normal sound levels.
4) May be worn for extensive periods.
5) Small and barely noticeable—suitable for young adults and workers in heavy industries.
6) Eliminates anticipating need to apply timely in special situations.

FIG. 1; Device
1) Fixed sonic sensor with on/off switch.
2) Disc battery.
3) Air holes
4) Wire coiled around the solid movable stem to form an electromagnetic solenoid placed within the cavity of the device.
5) Solid exterior sidewall of the cylindrical device.
6) Non-magnetic spring.
7) Centrally porous fixed ferrous/ferric disc.

Figure 2:
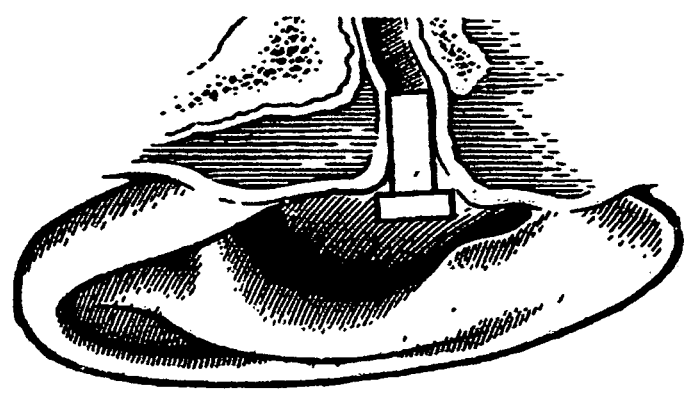

FIG. 2: Device inserted in outer ear canal.

What is claimed is:

1. A novel device, able to dampen transmission of loud external sounds to the auditory system but capable to conduct unaltered normal sounds when placed in the outer ear canal, comprising a) an inert cylinder with a central hole; b) a movable piston filling the central hole; c) a sound sensor; d) a battery for the electromagnet; e) an electromagnet formed by wires wound about the central piston which is activated by the sound sensor; f) a spring to lift the central piston when the electromagnet is not activated via reception of loud sounds by the sound sensor; and) a ferrous or ferric disk fixed at the bottom of the piston well, containing multiple air-passing holes centrally, to attract the piston when the electromagnet is activated, thereby closing the central hole to sound transmission.

* * * * *